(12) United States Patent
Ukawa

(10) Patent No.: US 8,712,493 B2
(45) Date of Patent: Apr. 29, 2014

(54) CARDIOPULMONARY RESUSCITATION MONITORING APPARATUS

(75) Inventor: Teiji Ukawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 114 days.

(21) Appl. No.: 13/416,318

(22) Filed: Mar. 9, 2012

(65) Prior Publication Data

US 2012/0232365 A1 Sep. 13, 2012

(30) Foreign Application Priority Data

Mar. 11, 2011 (JP) .................................. 2011-053955

(51) Int. Cl.
*A61B 5/1455* (2006.01)
*A61H 31/00* (2006.01)

(52) U.S. Cl.
USPC ............................................ 600/322; 601/41

(58) Field of Classification Search
USPC ..................... 600/310, 322, 323, 324; 601/41
See application file for complete search history.

(56) References Cited

U.S. PATENT DOCUMENTS

| | | | |
|---|---|---|---|
| 5,315,995 A | 5/1994 | Rivers | |
| 5,355,882 A | 10/1994 | Ukawa et al. | |
| 7,190,999 B2 * | 3/2007 | Geheb et al. | 601/41 |
| 2001/0047140 A1 * | 11/2001 | Freeman | 601/41 |
| 2004/0267324 A1 | 12/2004 | Geheb et al. | |
| 2004/0267325 A1 | 12/2004 | Geheb et al. | |
| 2006/0270952 A1 | 11/2006 | Freeman et al. | |
| 2008/0171311 A1 | 7/2008 | Centen et al. | |
| 2008/0269589 A1 | 10/2008 | Thijs et al. | |
| 2010/0076319 A1 | 3/2010 | Mannheimer et al. | |

FOREIGN PATENT DOCUMENTS

| | | |
|---|---|---|
| EP | 1491175 A1 | 12/2004 |
| JP | 5-207993 A | 8/1993 |
| JP | 6-86773 A | 3/1994 |
| JP | 3116252 B2 | 10/2000 |
| JP | 200546606 A | 2/2005 |
| JP | 2008-534083 A | 8/2008 |
| JP | 2009-501041 A | 1/2009 |

OTHER PUBLICATIONS

European Search Report dated Jun. 21, 2012 issued by the European Patent Office in counterpart European Application No. 12158349.6.
Office Action dated Nov. 22, 2013 issued by the Japanese Patent Office in corresponding Japanese Application No. 2011-053955.

* cited by examiner

*Primary Examiner* — Eric Winakur
(74) *Attorney, Agent, or Firm* — Sughrue Mion, PLLC

(57) ABSTRACT

A cardiopulmonary resuscitation monitoring apparatus includes: a light source section configured to cause light, which includes at least infrared light, to be incident on a living body; a light receiving unit configured to receive at least one of transmitted light that is transmitted through the living body and reflected light that is reflected from the living body; a calculating unit, based on DC components of received light intensities of the received light, configured to calculate a ratio of the DC components of the received light intensities of the received light during execution of cardiopulmonary resuscitation; an evaluating unit configured to perform evaluation related to the cardiopulmonary resuscitation based on the ratio calculated by the calculating unit; and an outputting unit configured to perform an output in accordance with a result of the evaluation performed by the evaluating unit.

7 Claims, 7 Drawing Sheets

CARDIOPULMONARY RESUSCITATION MONITORING APPARATUS

BACKGROUND OF THE INVENTION

The present invention relates to a cardiopulmonary resuscitation monitoring apparatus which, in order to enable a rescuer or the like to perform an optimum cardiac massage maneuver when, for example, cardiopulmonary resuscitation is executed, monitors effects of the maneuver.

In order to determine the adequateness of cardiopulmonary resuscitation (CPR) by measuring lung inflation due to the cardiopulmonary resuscitation, a technique using the thoracic impedance is employed. In the lung inflation measurement using the thoracic impedance, however, it is impossible to determine whether blood oxygenation and the blood flow status are improved or not.

On the other hand, a technique using SpO2 in order to monitor blood oxygenation during execution of cardiopulmonary resuscitation is known (see JP-A-2005-46606). During execution of cardiopulmonary resuscitation, however, pulse waves which are effective in a measurement of SpO2 cannot be obtained, and therefore the measurement is sometimes disabled. Moreover, a body motion due to cardiopulmonary resuscitation produces disturbances, and it is difficult to correctly perform the measurement.

It is known that the DC component of transmitted light has information of blood oxygenation, and this is effective in correction of noise contamination (see Japanese Patent No. 3,116,252). However, Japanese Patent No. 3,116,252 discloses only correction corresponding to noise contamination which temporarily occurs in a measurement of SpO2. In the reference, a situation where SpO2 cannot be obtained because pulse waves do not exist in a state where cardiopulmonary resuscitation must be performed is not considered.

SUMMARY

It is therefore an object of the invention to provide a cardiopulmonary resuscitation monitoring apparatus which monitors effects of a maneuver so that a rescuer or the like can perform an optimum cardiac massage maneuver.

In order to achieve the object, according to the invention, there is provided a cardiopulmonary resuscitation monitoring apparatus comprising: a light source section configured to cause light, which includes at least infrared light, to be incident on a living body; a light receiving unit configured to receive at least one of transmitted light that is transmitted through the living body and reflected light that is reflected from the living body; a calculating unit, based on DC components of received light intensities of the received light, configured to calculate a ratio of the DC components of the received light intensities of the received light during execution of cardiopulmonary resuscitation; an evaluating unit configured to perform evaluation related to the cardiopulmonary resuscitation based on the ratio calculated by the calculating unit; and an outputting unit configured to perform an output in accordance with a result of the evaluation performed by the evaluating unit.

The light caused to be incident on the living body may further include red light, and the ratio calculated by the calculating unit may be a ratio of DC components of received light intensities of the infrared light and DC components of received light intensities of the red light, during the execution of the cardiopulmonary resuscitation.

The evaluation related to the cardiopulmonary resuscitation may be evaluation related to a rise of blood oxygen saturation.

The light caused to be incident on the living body may include only the infrared light, the ratio calculated by the calculating unit may be a ratio of DC components of received light intensities of the infrared light during the execution of the cardiopulmonary resuscitation, and the evaluation performed by the evaluating unit based on the calculated ratio may be evaluation of a blood flow increase.

The infrared light may have a wavelength in a vicinity of 805 nm.

The ratio may be calculated by using the Lambert-Beer Law.

The light source and the light receiving unit may constitute a pulse oximeter probe.

DETAILED DESCRIPTION OF EMBODIMENTS

Figure 1:
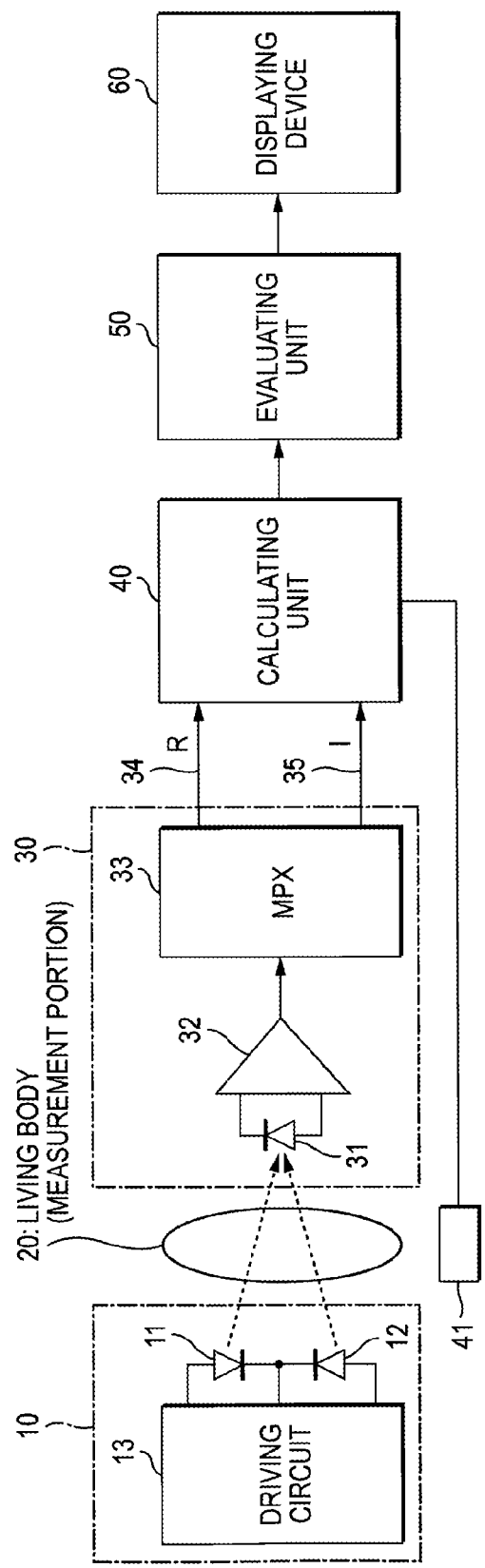
FIG. 1 is a block diagram showing the configuration of a first embodiment of the cardiopulmonary resuscitation monitoring apparatus of the invention.

Hereinafter, embodiments of the cardiopulmonary resuscitation monitoring apparatus of the invention will be described with reference to the accompanying drawings. In the figures, the identical components are denoted by the same reference numerals, and duplicated description will be omitted. FIG. 1 shows an embodiment of the cardiopulmonary resuscitation monitoring apparatus of the invention. The apparatus includes a light source section 10 which causes at least infrared light to be incident on a living body. In the light source section 10, a light emitting diode 11 which emits red light, and a light emitting diode 12 which emits infrared light are disposed. For example, the wavelength of the red light can be set to 660 nm, and that of the infrared light can be set to 900 nm, 805 nm, or a range of plus and minus 5 nm relative to 805 nm.

A driving circuit 13 is connected to the light emitting diodes 11, 12. For example, the driving circuit 13 alternately supplies a current to the light emitting diodes 11, 12 to cause the diodes to emit light. A photodiode 31 constituting a light receiving unit 30 is disposed on the side which is opposed to the light emitting diodes 11, 12 across the living body (measurement portion) 20. The photodiode 31 receives the red light and the infrared light, converts them to light receiving signals of respective corresponding voltages by photoelectric conversion, and sends the signals to an amplifier 32. The light source section 10 and the light receiving unit 30 may be integrally configured as a probe of a pulse oximeter. The signals which are amplified by the amplifier 32 are sent to a multiplexer (MPX) 33. Then, the DC component R of the light receiving signal of the red light is sent to a calculating unit 40 through a signal line 34, and the DC component I of the light receiving signal of the infrared light is sent to the calculating unit 40 through a signal line 35.

An evaluating unit 50 is connected to the calculating unit 40. These units may be configured by a computer. In this case, digitized DC components are used. Based on the DC component of the incident light intensity, and the DC component of the received light intensity, the calculating unit 40 calculates a ratio of DC components of the received light intensities during execution of cardiopulmonary resuscitation.

Figure 2:
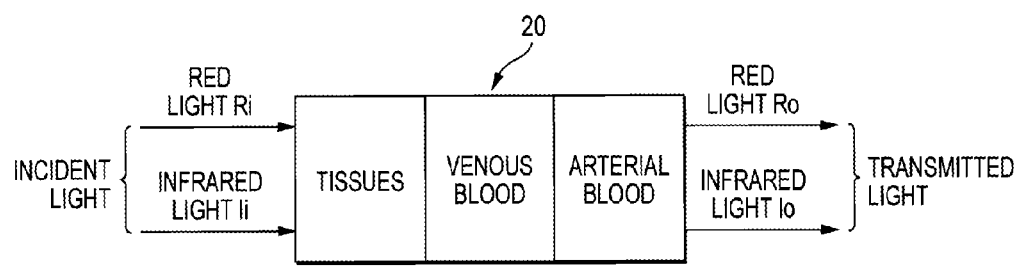
FIG. 2 is a view illustrating the principle of application of the Lambert-Beer Law by the embodiment of the cardiopulmonary resuscitation monitoring apparatus of the invention.

The incident light incident on the living body (measurement portion) 20, and the received light (i.e., light which is transmitted through the living body and/or light reflected in the living body) will be described. As shown in FIG. 2, the living body (measurement portion) 20 is divided into arterial blood, venous blood, and other tissues. With respect to the incident light intensity Ri of the red light, the received light intensity Ro is obtained, and, with respect to the incident light intensity Ii of the infrared light, the received light intensity Io is obtained.

Figure 3:
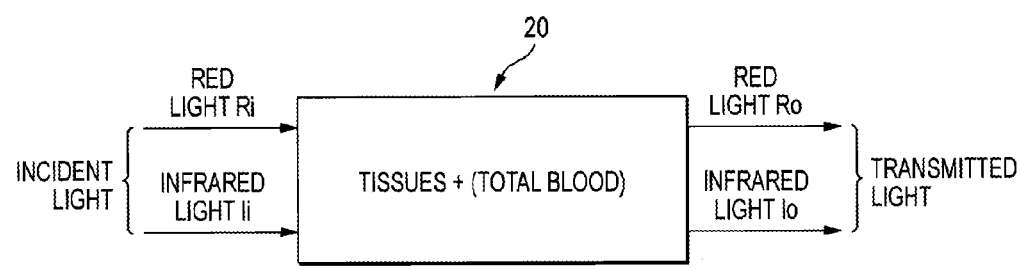
FIG. 3 is a view illustrating the principle of application of the Lambert-Beer Law by the embodiment of the cardiopulmonary resuscitation monitoring apparatus of the invention.

For the sake of convenience, also in the case of FIG. 3 where the arterial blood, the venous blood, and the other tissues are considered to be integrated with one another, the received light intensity Ro is obtained with respect to the incident light intensity Ri of the red light, and the received light intensity Io is obtained with respect to the incident light intensity Ii of the infrared light. In this way, the Lambert-Beer Law is applied.

During a series of executions of cardiopulmonary resuscitation, with respect to the red light, the followings are set:

ER: absorption coefficient of tissues+total blood for the red light;
C: coefficient related to the concentration of tissues+total blood; and
D: thickness of tissues+total blood.

During a series of execution of cardiopulmonary resuscitation, with respect to the infrared light, the followings are set:

EI: absorption coefficient of tissues+total blood for the infrared light;
C: coefficient related to the concentration of tissues+total blood; and
D: thickness of tissues+total blood.

When the Lambert-Beer Law is applied, $$\ln(Ri/Ro) = ER \ast C \ast D \quad\text{(Exp. 1)}$$

$$\ln(Ii/Io) = EI \ast C \ast D \quad\text{(Exp. 2)}.$$

The coefficient C is constant before and after execution of cardiopulmonary resuscitations. When a change due to a series of executions of cardiopulmonary resuscitations is indicated by adding a prime symbol ('), therefore, the followings are obtained:

$$\ln(Ri/Ro') = ER' \ast C \ast D' \quad\text{(Exp. 3)}$$

$$\ln \ast Ii/Io') = EI' \ast C \ast D' \quad\text{(Exp. 4)}.$$

When Exp. 2 is subtracted from Exp. 1 ((Exp. 1)−(Exp. 2)), $$\ln(Ri/Ii) - \ln(Ro/Io) = (ER-EI) \ast C \ast D \quad\text{(Exp. 5)}.$$

When Exp. 4 is subtracted from Exp. 3 ((Exp. 3)−(Exp. 4)), $$\ln(Ri/Ii) - \ln(Ro'/Io') = (ER'-EI') \ast C \ast D' \quad\text{(Exp. 6)}.$$

When it is assumed that the thickness change is negligible with respect to the total thickness, D/D'=1 is attained, and also C is constant, the following is obtained:

$$\ln((Ro'/Io')/(Ro/Io)) = ((ER-EI)-(ER'-EI')) \ast D \ast C \quad\text{(Exp. 7)}.$$

When the logarithmic representation is returned to the exponential representation, $$(Ro'/Io')/(Ro/Io) = \mathrm{Exp}((ER-EI)-(ER'-EI')) \ast D \ast C) \quad\text{(Exp. 8)}.$$

The calculating unit 40 sends the above calculation result to the evaluating unit 50. By referring to, for example, an output of a pressure sensor 41 (for example, placed in a portion where pressurization is performed) connected to the calculating unit 40, it is possible to determine whether pressurization by cardiopulmonary resuscitation is being performed and signals with a prime symbol (') are obtained, or whether the pressurization is not being performed and signals without a prime symbol (') are obtained. The evaluating unit evaluates cardiopulmonary resuscitation based on the calculated ratio of DC components of the received light intensities and/or the levels of the received light intensities. In the embodiment, the evaluation is performed based on the following discussion.

Since the absorption coefficient of the tissue is constant before and after execution of cardiopulmonary resuscitation, ER and EI reflect the blood absorption coefficient. When the blood oxygen saturation is raised, the absorption coefficient ER for the red light is decreased, and the absorption coefficient EI for the infrared light is increased (however, the increase of EI is small as compared with the decrease of ER). From (Exp. 8), it is known that, when the blood oxygen saturation is raised, Exp ((ER−EI)−(ER'−EI')) is increased. Therefore, (Ro'/Io')/(Ro/Io) which is the left-hand side of (Exp. 8) is increased.

Figure 4:
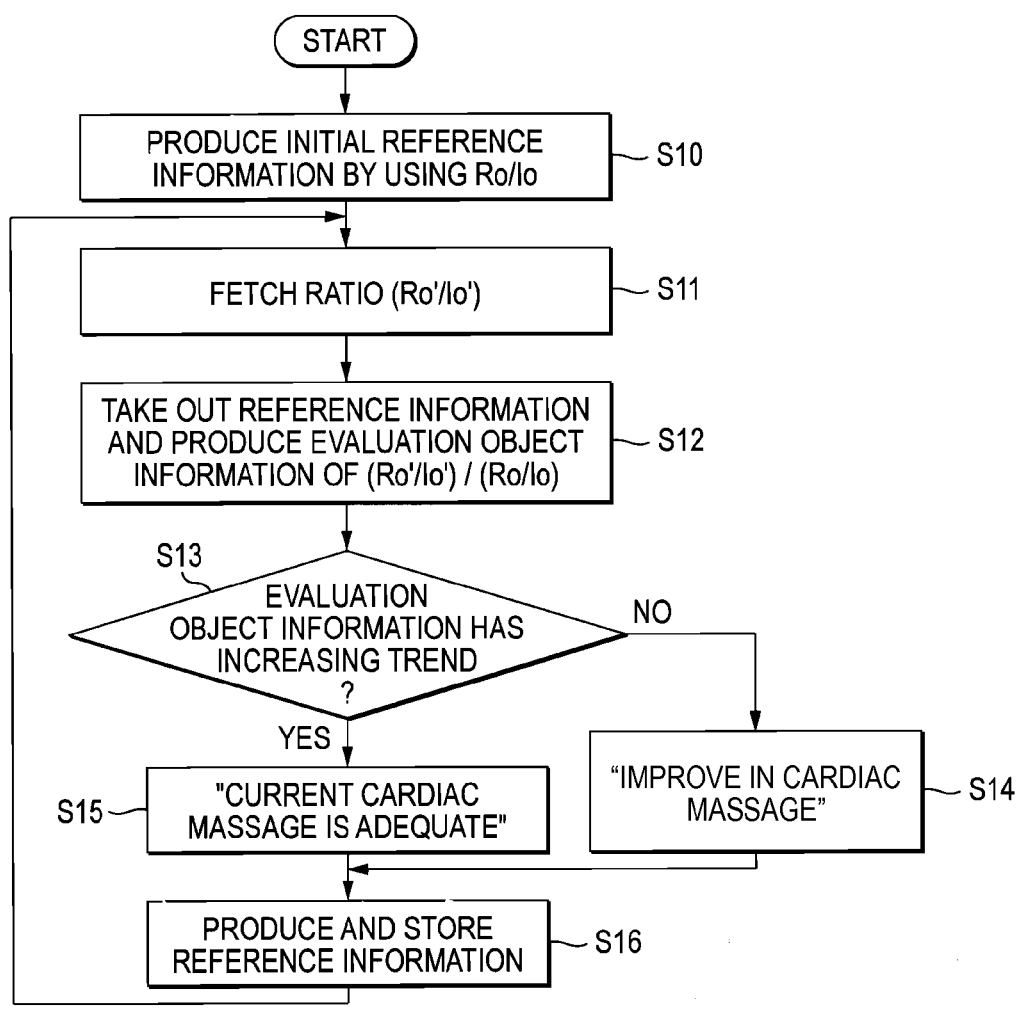
FIG. 4 is a flowchart illustrating the operation of the first embodiment of the cardiopulmonary resuscitation monitoring apparatus of the invention.

Therefore, the evaluating unit 50 operates in accordance with the flowchart shown in FIG. 4. First, initial reference information is produced by using past (Ro/Io) in the state of execution of cardiopulmonary resuscitation (S10), (Ro'/Io') which is the ratio of DC components of the received light intensities is fetched (S11), the reference information which is produced in step S10 is taken out to produce evaluation object information of (Ro'/Io')/(Ro/Io) (S12), and it is determined whether the evaluation object information has an increasing trend or not (S13). If NO, message information of "Improve in cardiac massage" is sent to a displaying device 60 which is an outputting unit, to be displayed thereon (S14).

If YES in step S12, message information of "Current cardiac massage is adequate" is sent to the displaying device 60 which is an outputting unit, to be displayed thereon (S15). In succession to step S15, reference information is produced by using current (Ro'/Io'), and stored (S16). Then, the process returns to step S11.

Figure 7:
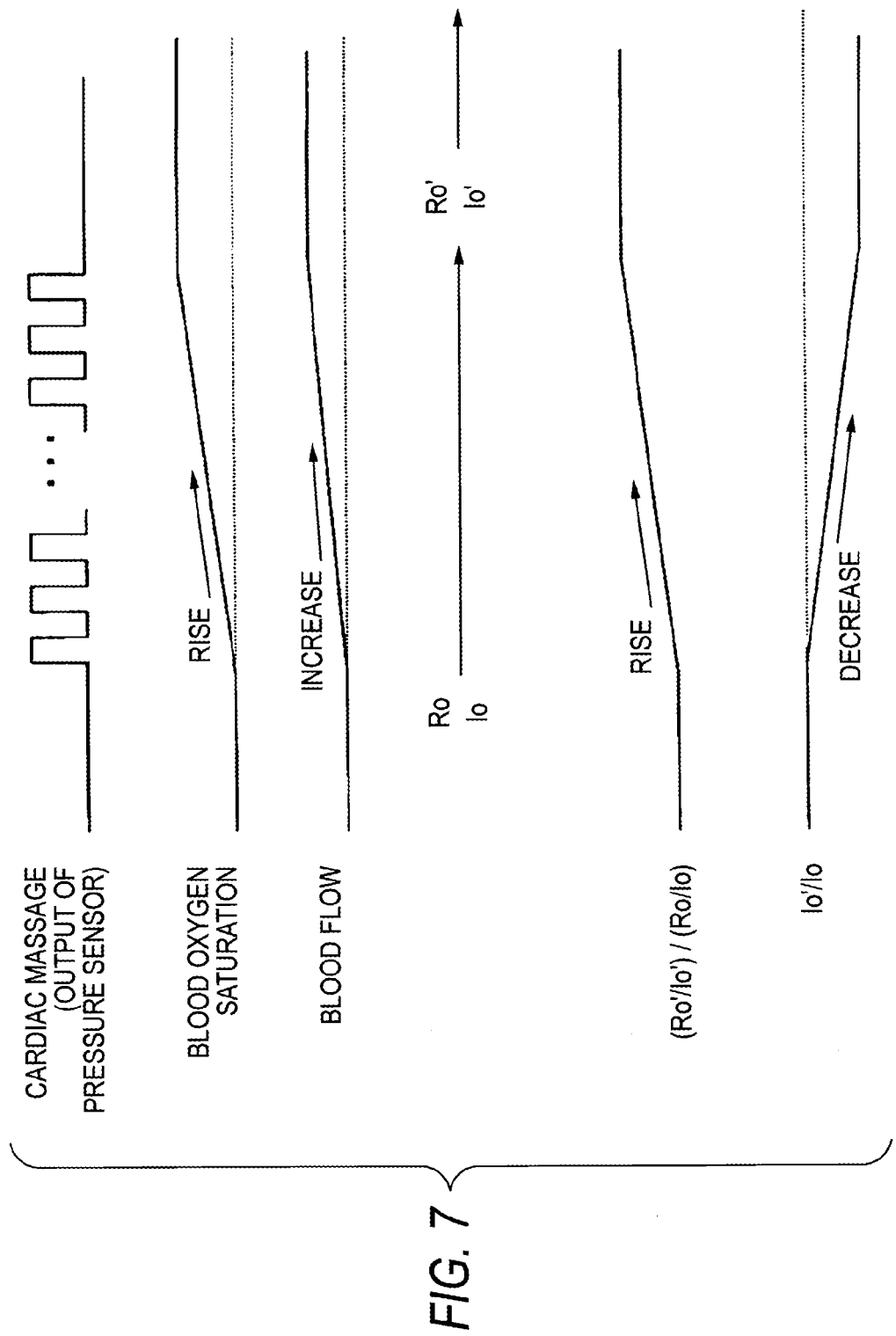
FIG. 7 is a view showing temporal transitions of the blood oxygen saturation, blood flow, and signals during cardiopulmonary resuscitation.

As the reference information, (Ro/Io) which is currently used may be set as it is, or (Ro'/Io') which was obtained in the N-th (N is an integer) past operation may be set as it is. Alternatively, a value (for example, the average value, the intermediate value, or the mode value) which is obtained by using ratios ranging from current (Ro'/Io') to (Ro'/Io') in the N-th (N is an integer) past operation may be set as the reference information. Moreover, Ro/Io before the start of cardiopulmonary resuscitation may be used as fixed reference information. FIG. 7 shows temporal transitions of the blood oxygen saturation, blood flow, and signals during cardiopulmonary resuscitation. From Ro and Io before cardiopulmonary resuscitation (cardiac massage), and Ro' and Io' which are obtained by performing cardiopulmonary resuscitation (cardiac massage) a plurality of times (for example, 30 times), it is seen that the blood flow is increased, the blood oxygen saturation is raised, and, in this case, also (Ro'/Io')/(Ro/Io) is raised. As the value of Ro'/Io', a value which is obtained each time when cardiopulmonary resuscitation (cardiac massage) is performed may be employed, or a value (for example, the average value, the intermediate value, or the mode value) which is obtained by performing cardiopulmonary resuscitation (cardiac massage) a plurality of times (for example, 30 times) may be of course employed.

The displaying device 60 which is an outputting unit may be a device that shows characters by means of display such as an LCD, or a device which outputs a message simply by lighting, that which outputs a message by means of an audio output, or that which outputs a message by a necessary combination of these means. The displaying device may be any kind of device as far as it can perform an output showing the evaluation by the evaluating unit 50.

Figure 5:
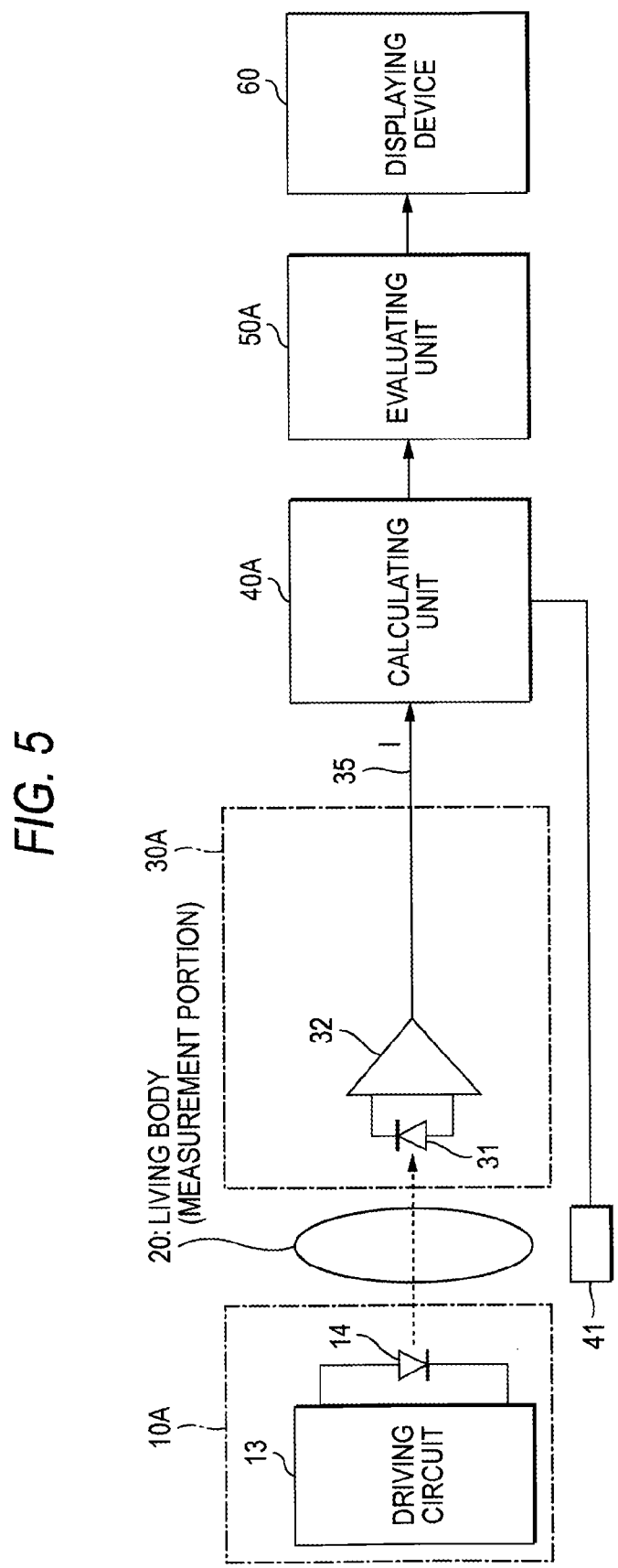
FIG. 5 is a block diagram showing the configuration of a second embodiment of the cardiopulmonary resuscitation monitoring apparatus of the invention.

FIG. 5 is a diagram of a cardiopulmonary resuscitation monitoring apparatus of a second embodiment. In the embodiment, only a light emitting diode 14 which emits infrared light is used in a light source section 10A. The light emitted from the light emitting diode 14 may have a wavelength of 805 nm. Alternatively, a configuration where the light source section 10A selects the wavelength of 805 nm may be employed. Here, the wavelength is not limited to this value, "805 nm" may mean the vicinity of 805 nm, or infrared light in a range of plus and minus 5 nm relative to 805 nm may be used.

The above-described configuration is used for preventing the EI from being affected by the blood oxygen saturation. According to the configuration, a change of the EI due to the blood oxygen saturation can be made smaller than that of the ER, and the EI can be deemed to be constant. In addition to the above-described configuration, the multiplexer 33 in FIG. 1 is not disposed in a light receiving unit 30A. The DC component I of the light receiving signal of the infrared light is sent to a calculating unit 40A through the signal line 35.

Since the monitoring apparatus has the configuration where the EI can be deemed to be constant (EI'=EI) as described above, the calculating unit 40A obtains a difference of (Exp. 4)−(Exp. 2).

The difference of (Exp. 4)−(Exp. 2) is expressed as:

$$\ln(Ii/Io')-\ln(Ii/Io)=EI*C*(D'-D) \quad (\text{Exp. 9}).$$

When (Exp. 9) is rearranged, $$-\ln(Io'/Io)=EI*C*(D'-D) \quad (\text{Exp. 10}).$$

When the logarithmic representation is converted to the exponential representation, $$Io'/Io=\mathrm{Exp}(-EI*C*(D'-D)) \quad (\text{Exp. 11}).$$

The calculating unit 40 sends the calculation result of (Exp. 11) above to an evaluating unit 50A. When the blood flow is improved and D'>D is attained, the right-hand side of (Exp. 11) is decreased. Namely, the left-hand side of (Exp. 11), i.e., the received light intensity ratio (Io'/Io) of the infrared light is decreased. When the received light intensity of the infrared light is temporally measured, the increasing/decreasing trend of the blood flow can be estimated.

Figure 6:
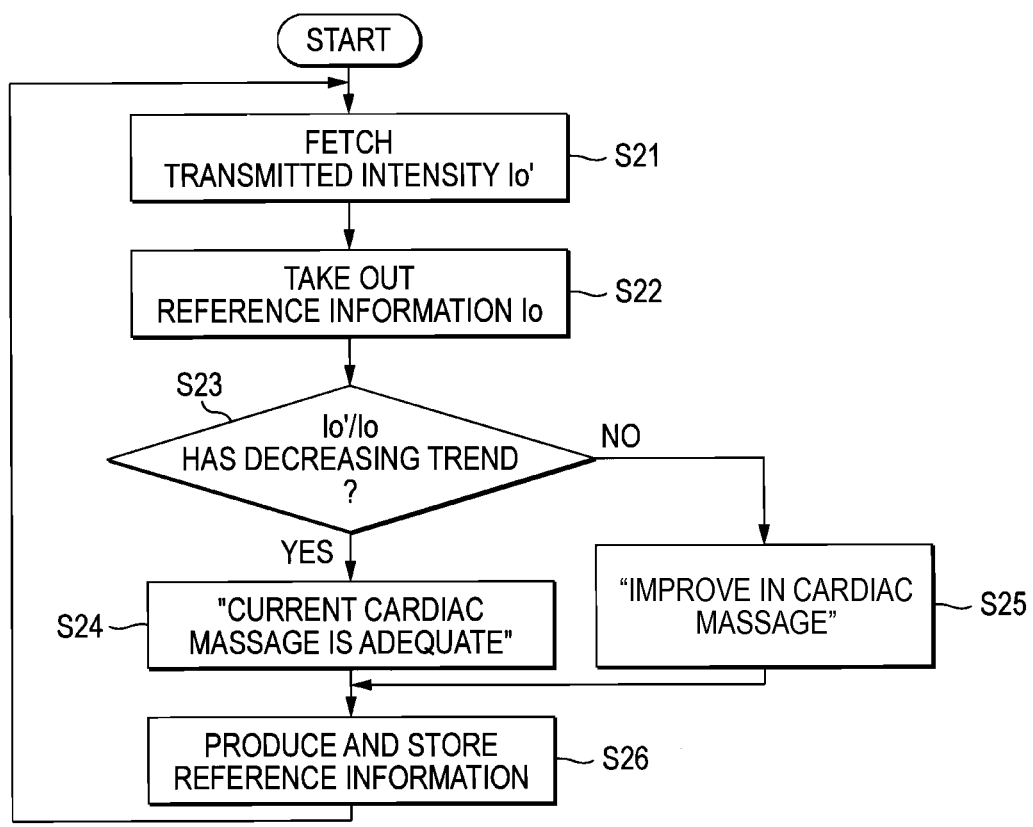
FIG. 6 is a flowchart illustrating the operation of the second embodiment of the cardiopulmonary resuscitation monitoring apparatus of the invention.

Therefore, the evaluating unit 50A operates in accordance with the flowchart shown in FIG. 6. The received light intensity Io' of the infrared light is fetched (S21), reference information which is produced by using past Io in the state of execution of cardiopulmonary resuscitation is taken out (S22), and it is determined whether their ratio has a decreasing trend or not (S23). If YES, the message information of "Current cardiac massage is adequate" is sent to the displaying device 60 which is an outputting unit, to be displayed thereon (S24).

If NO in step S22, the message information of "Improve in cardiac massage" is sent to the displaying device 60 which is an outputting unit, to be displayed thereon (S25). In succession to step S25, reference information is produced by using current Io', and stored (S26). Then, the process returns to step S21.

As the next reference information, current Io' may be set as it is. Alternatively, the average of intensities ranging from current Io' to Io' in the N-th (N is an integer) past operation may be set as the reference information. Moreover, Io' before the start of cardiopulmonary resuscitation may be used as fixed reference information. FIG. 7 shows temporal transitions of the blood oxygen saturation, blood flow, and signals during cardiopulmonary resuscitation. From Io before cardiopulmonary resuscitation (cardiac massage), and Io' which are obtained by performing cardiopulmonary resuscitation (cardiac massage) a plurality of times (for example, 30 times), it is seen that the blood flow is increased, the blood oxygen saturation is raised, and, in this case, Io'/Io is decreased.

In the second embodiment described above, the adequateness of cardiac massage may be evaluated by using only the received light intensity of the infrared light and referring its temporal change, or without using the received light intensity of the infrared light. Alternatively, the adequateness of cardiac massage may be evaluated by using the ratio and/or received light intensities which are used in the first embodiment.

According to an aspect of the invention, based on the DC component of the incident light intensity of infrared light incident on the living body, and the DC component of the received light intensity of the received light, the ratio of DC components of the received light intensities during execution of cardiopulmonary resuscitation is calculated, and evaluation related to cardiopulmonary resuscitation is performed based on the calculated ratio of DC components of the received light intensity and/or the level of the received light intensity. By using the DC component of the received light having information of blood oxygenation, the increasing/decreasing trend of the blood oxygen saturation can be estimated depending on the level of the received light intensity. The trend of blood oxygenation is measured in accordance with the ratio of the DC component of the received light intensity, and a cardiac massage maneuver by a rescuer or the like can be guided so as to be properly performed.

Figure 8:
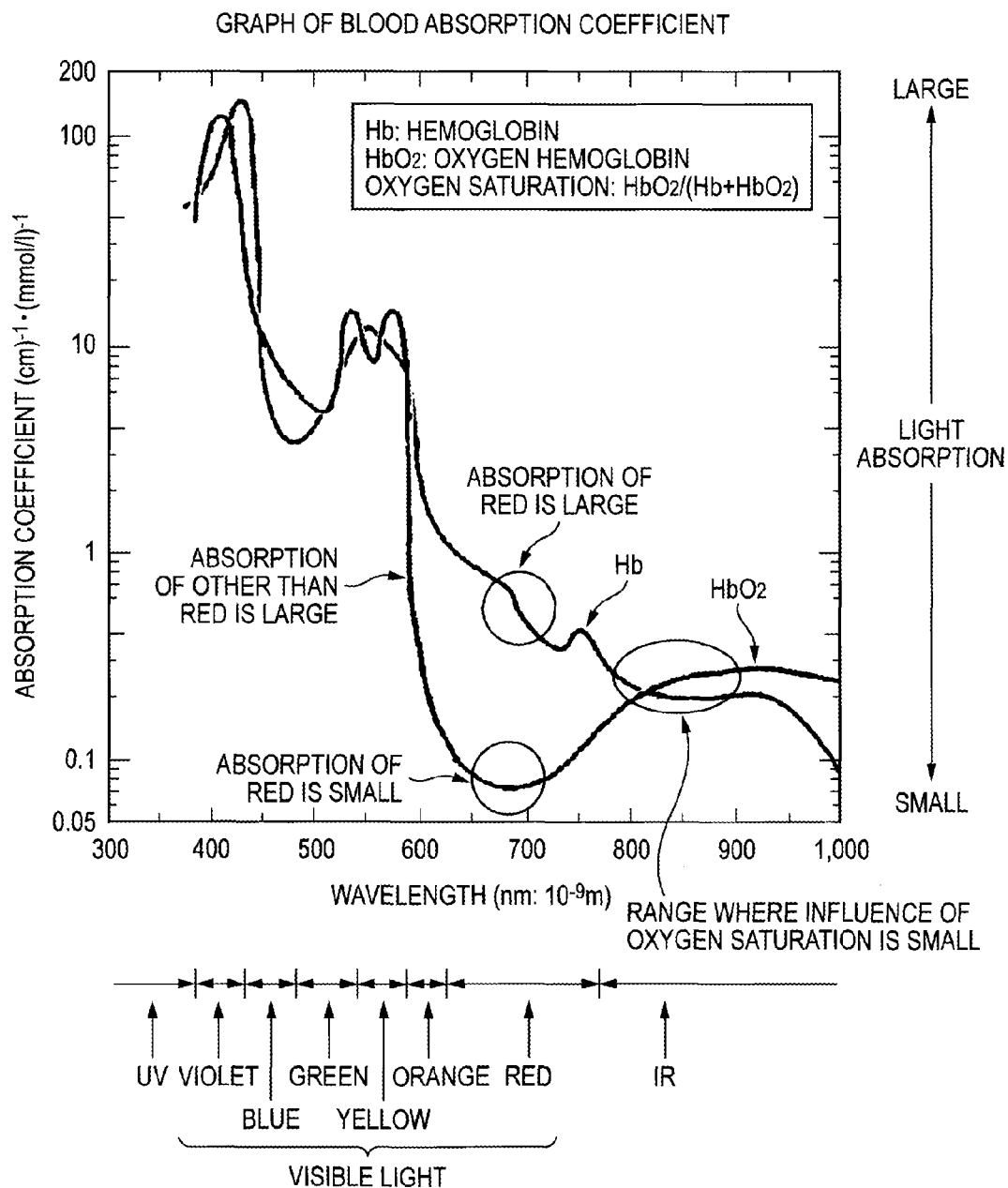
FIG. 8 is a view showing the light absorption characteristics of blood.

A change of the blood absorption coefficient due to the oxygen saturation is largest in the red region, and small in the infrared region of 800 nm or longer. In the vicinity of 805 nm, particularly, the absorption coefficient is constant irrespective of the oxygen saturation. FIG. 8 shows the light absorption characteristics of blood. According to as aspect of the invention, infrared light in the vicinity of 805 nm (for example, a range of plus and minus 5 nm relative to 805 nm) is used. Therefore, the infrared absorption coefficient EI of blood can be set to be constant, and a correct measurement of the increasing/decreasing trend of the blood flow by using only infrared light is enabled. Not only in the vicinity of 805 nm, but also in the infrared region of 800 nm or longer, the EI can be deemed to be substantially constant, and the increasing/decreasing trend of the blood flow can be known.

What is claimed is:

1. A cardiopulmonary resuscitation monitoring apparatus comprising:
   a light source section configured to cause light, which includes at least infrared light, to be incident on a living body;
   a light receiving unit configured to receive at least one of transmitted light that is transmitted through the living body and reflected light that is reflected from the living body;
   a calculating unit, based on DC components of received light intensities of the received light, configured to calculate a ratio of the DC components of the received light intensities of the received light during execution of cardiopulmonary resuscitation;
   an evaluating unit configured to perform evaluation related to the cardiopulmonary resuscitation based on the ratio calculated by the calculating unit; and
   an outputting unit configured to perform an output in accordance with a result of the evaluation performed by the evaluating unit.

2. The cardiopulmonary resuscitation monitoring apparatus according to claim 1, wherein:
   the light caused to be incident on the living body further includes red light; and
   the ratio calculated by the calculating unit is a ratio of DC components of received light intensities of the infrared light and DC components of received light intensities of the red light, during the execution of the cardiopulmonary resuscitation.

3. The cardiopulmonary resuscitation monitoring apparatus according to claim 2, wherein the evaluation related to the cardiopulmonary resuscitation is evaluation related to a rise of blood oxygen saturation.

4. The cardiopulmonary resuscitation monitoring apparatus according to claim 1, wherein:
   the light caused to be incident on the living body includes only the infrared light;
   the ratio calculated by the calculating unit is a ratio of DC components of received light intensities of the infrared light during the execution of the cardiopulmonary resuscitation; and
   the evaluation performed by the evaluating unit based on the calculated ratio is evaluation of a blood flow increase.

5. The cardiopulmonary resuscitation monitoring apparatus according to claim 1, wherein the infrared light has a wavelength in a vicinity of 805 nm.

6. The cardiopulmonary resuscitation monitoring apparatus according to claim 1, wherein the ratio is calculated by using the Lambert-Beer Law.

7. The cardiopulmonary resuscitation monitoring apparatus according to claim 1, wherein the light source and the light receiving unit constitute a pulse oximeter probe.

* * * * *